United States Patent [19]

Pang et al.

[11] 4,431,743

[45] * Feb. 14, 1984

[54] METHOD FOR DETERMINING STEROIDS IN HUMAN BODY LIQUIDS

[75] Inventors: Songja Pang; Maria New, both of New York, N.Y.

[73] Assignee: Cornell Research Foundation, Inc., Ithaca, N.Y.

[*] Notice: The portion of the term of this patent subsequent to Oct. 28, 1997 has been disclaimed.

[21] Appl. No.: 201,589

[22] Filed: Oct. 28, 1980

Related U.S. Application Data

[63] Continuation-in-part of Ser. No. 887,326, Mar. 16, 1978, abandoned.

[51] Int. Cl.³ .................. G01N 33/56; G01N 33/58; G01N 33/60; G01N 33/52
[52] U.S. Cl. .................. 436/542; 436/539; 436/804; 436/811; 436/817
[58] Field of Search .............. 424/1, 12; 23/230 B; 436/542, 539, 804, 811, 817

[56] References Cited

U.S. PATENT DOCUMENTS

| | | | |
|---|---|---|---|
| 4,157,895 | 6/1979 | Finlay et al. | 424/1 |
| 4,230,684 | 10/1980 | Pang et al. | 424/1 |
| 4,299,812 | 11/1981 | Coombes | 424/1 |
| 4,337,065 | 6/1982 | Hiratsuka et al. | 422/56 |

OTHER PUBLICATIONS

Sekihara et al., Steroids, 20:6, (1972), 813–824.
Smith et al., Clin. Chem. Acta, 65, (1975), 5–13.
Pang et al., J. Lab. Clin. Med., 95, (Apr. 1980), 515–524.

*Primary Examiner*—Christine M. Nucker
*Attorney, Agent, or Firm*—Schwartz, Jeffery, Schwaab, Mack, Blumenthal & Koch

[57] ABSTRACT

A method for determination of a steroid such as dehydroepiandrosterone sulfate (DS) in a sample of a human body liquid wherein the liquid sample is transferred to a sheet of microfilter paper and dried before being treated with an aqueous solvent to obtain a mixture wherein the dried body liquid is substantially redissolved in the aqueous solution. The mixture is contacted with an aqueous solution of an agent capable of selectively binding the steroid in the presence of a radioisotopically labeled form of steriod whereby part of the labeled steroid and part of the unlabeled steroid present in the sample are bound by forming a complex with the binding agent. Bound steroids are separated from unbound steroids in the aqueous solution and the radioactivity of at least the separated binding agent-steroids-complex or the unbound steroids is performed to determine the concentration of the hormone as a function of measured radioactivity. Additionally, a means for performing the method is disclosed.

13 Claims, No Drawings

METHOD FOR DETERMINING STEROIDS IN HUMAN BODY LIQUIDS

The invention described herein was made in the course of work under a grant from the Department of Health, Education and Welfare, Grant No. R01 HD00072.

This is a continuation-in-part of copending patent application Ser. No. 887,326, filed Mar. 16, 1978, abandoned and incorporated herein by reference.

The present invention relates to a micro-method and means for the determination of steroids, in particular of dehydroepiandrosterone sulfate (DS), in human body liquids and to a new method and means for detection of abnormal adrenal androgen secretion in the differential diagnosis of excess or deficient androgen producing conditions (e.g., virilism, hirsutism, male precocious puberty or delayed puberty). Recently radioimmunoassay for the measurement of dehydroepiandrosterone sulfate has become available. The usefulness of this assay for the diagnosis of abnormal puberty has been established, (See, e.g., Korth-Schutz S, Levine LS, and New MI: Dehydroepiandrosterone sulfate (DS) levels, a rapid test for abnormal adrenal secretion. J. Clin. Endocrinol Metab 42: 1005,1976.). However, the prior art method for the determination of steroids involves the analysis of blood plasma and requires relatively large amounts of blood for the separation of the blood cell mass from the plasma. Further, sample collection by veno puncture is inconvenient in small infants.

In the recently developed radioimmunoassays (RIA), radiological means are employed to detect and/or measure the presence of a steroid in the patient's blood (or urine). In these radioimmunoassay tests, a solution of an antibody of the steroid is placed in contact with a mixture of the steroid, which has been extracted from a sample of the patient's body fluid to be tested and a known amount of the same steroid tagged with a radioactive isotope. The steroid in the test sample and the labeled steroid compete for interaction with the steroid antibody. The resulting steroids-antibody-complex is then separated from the fluid and either fraction may be analyzed radiologically in order to determine the respective proportions of the labeled and unlabeled steroid which became bound to the antibody. The concentration of steroid in the sample can be calculated from this information, since the proportion of labeled and unlabeled steroid will be in the same proportion in both fractions. The radioimmunoassay techniques exhibit a high degree of accuracy and specificity. Until recently the radioimmunoassay techniques required relatively large amounts of blood for the preliminary separation of blood plasma from the hematocrit, and also have the usual disadvantage that samples can be stored only at low temperature, since the liquid samples are easily infected and spoiled by growth of bacteria.

A new method developed and applied to the determination of 17α-hydroxy-progesterone for screening patients with congenital adrenal hyperplasia utilizes eluates of whole blood collected on filter paper. (Pang S., Hotchkiss J., Drash A. L., Levine L. S. and New. M.I.: Microfilter Paper Method for 17α-Hydroxyprogesterone Radioimmunoassay: Its Application for Rapid Screening for Congenital Adrenal Hyperplasia, J. Clin. Endocrinol. Metab. 45, 1003, 1977.). This method has the specificity, accuracy and precision of RIA in whole plasma. Further, it has been shown that concentrations of 17α-hydroxy-progesterone remain unchanged in dried filter paper blood samples when stored at room temperature for 21 days and, therefore, the filter paper with dried blood may be sent for steroid assay by mail. Although this approach overcomes many of the deficiencies of the prior art, the method includes an extraction step requiring the use of a volatile organic solvent necessary to isolate the steroid of interest. Additionally, a subsequent step requires separation of the residue from the organic solvent. These extra steps take time, can reduce yield and expose lab technicians to the hazards arising from the use of a volatile organic solvent.

SUMMARY OF THE INVENTION

It is an object of the present invention to provide a method for the determination of steroid hormones, in particular dehydroepiandrosterone sulfate in small samples of human body liquids collected on a sample absorbing sheet (e.g., filter paper), in particular, small blood samples, which avoids the disadvantages of the prior art methods.

It is a special object of the present invention, to provide such a method which can be rapidly performed and requires only minute amounts of blood which can be easily obtained, e.g., from the finger tip or with heel prick in small children.

It is a further object of the present invention to provide such a method for determining the dehydroepiandrosterone sulfate blood level of newborn infants.

It is a further object of the present invention to provide such a method, wherein the blood sample can easily be obtained by a practicing physician and then be mailed to steroid laboratories in medical centers, obviating the need for frozen storage, centrifugation, and special containers.

It is a further object of the present invention to provide a method for the determination of steroids in human body liquids, which is especially suited for surveying ambulatory patients.

In order to accomplish the foregoing objects according to the present invention, there is provided a method for determination of a steroid in a sample of a human body liquid, which comprises the steps of:

(a) transferring said liquid sample onto a sheet of material (e.g., filter paper) which is capable of uniformly absorbing said liquid sample;

(b) drying the sample-containing sheet;

(c) treating a portion of the dry sample-containing sheet, which is equivalent to a predetermined amount of the sample with an aqueous solvent in order to obtain a mixture wherein the dried blood is substantially redissolved in the aqueous solvent;

(d) contacting said mixture containing the steroid with an aqueous solution of an agent, capable of selectively binding said steroid in the presence of a radioisotopically labeled steroid, whereby part of said labeled steroid and part of said unlabeled steroid, present in the sample, are bound by forming a complex with said binding agent. Following this step said bound steroids are separated from unbound steroids in said aqueous solution and the radioactivity of at least said separated binding agent-steroids-complex or said unbound steroids is measured to determine the concentration of said hormone as a function of the measured radioactivity.

The steroid-binding agent, which is employed in the method according to the present invention, for determining steroids in human body fluids, may be any reagent conventionally employed in immuno chemical methods, in particular antisera for the respective steroids which are conventionally used in radioimmunoassays. The preparation of antisera for the various steroid hormones is well known in the art and these antisera are commercially available. In applying this method for the determination of dehydroepiandrosterone sulfate in blood samples, the conventional antiserum for dehydroepiandrosterone sulfate is used.

The radioisotopically labeled steroid, which is used as an indicating means, may comprise different radioactive isotopes, e.g., $^3H$ or $^{14}C$. For measuring the radioactivity, a conventional liquid scintillation counter, which is adapted for beta-counting, can be used.

The method for determining steroids according to the present invention, using only extremely small amounts of human body liquids, is especially suited for detecting unduly high amounts of steroid hormones in the human body and provides a simple means for detecting disorders in the body functions which are characterized by increased levels of steroids in the body, for example, hirsutism, virilism and disorders of puberty, etc.

The method for determining dehydroepiandrosterone sulfate in a small blood sample according to the present invention is particularly suitable as a rapid screening test for adnormal adrenal androgen secretion in differential diagnosis of virilization in childhood or in adults.

Further objects, features, and advantages of the present invention will become apparent from the detailed description of the invention and its preferred embodiments, which follows.

DETAILED DESCRIPTION OF THE INVENTION

In accordance with the present invention, there has been discovered a novel micromethod for determining the concentration of specific steroids in human body liquids, in particular, in small samples of whole blood. According to the present invention, a small amount of a human body liquid, in particular human whole blood, is collected on a sheet of absorbing material, preferably a standard filter paper, from which the steroid can later be eluted. The amount of steroid, which is recovered from the eluate, is then determined in a conventional radioimmunoassay. The method of applying a small blood sample on a filter paper is a standard hospital procedure in the screening for phenylketonurea in newborns and has also been used for screening neonates for hypothyroidism (see Larsen et al, Pediatr. Res. 9, 604, 1975). Yet, such a method of collecting a blood sample on a filter paper with subsequent elution of the blood from the filter paper, has never been used in connection with the process of extracting a steroid-containing fraction from blood samples and measurements of the steroid-content by radioimmunoassay.

It has now been found that the steroid content in a whole blood sample which has been absorbed and dried on an absorbing paper remains unchanged even if the blood-containing paper is stored at room temperature for a period of up to about one month. Even after such a long period of storage, the steroid-content of the blood sample can be completely recovered from the absorbing paper by elution of the dried blood-containing paper with an aqueous solution. For example, an excellent correlation has been found between the values of dehydroepiandrosterone sulfate obtained from blood samples of various subjects which were treated by a micro-filter-paper-method according to the present invention, and the values from plasma samples of whole blood samples, which were treated in a conventional procedure for radioimmunoassay tests in these same subjects.

In addition, blood samples on filter paper can easily be sent by surface mail by physicians practicing in geographically isolated areas to steroid laboratories in medical centers, obviating the need for frozen storage, centrifugation, and special containers. The method is suitable for the survey of ambulatory patients. In such situations, the family doctor could easily screen for a number of conditions and disorders, particularly for excessive steroid production, e.g., virilism of all kinds, Cushings syndrome, and possibly some adrenal and pituitary steroid deficient states. The presently claimed method is easy and rapid and has the specificity, accuracy, and precision of radioimmunoassays in whole plasma. The minute amount of blood which is required, the simplicity of sample collection which can be easily performed by heel prick, and the ease with which samples may be transported, make this method highly useful for large scale screenings.

Summarizing the foregoing, the micromethod, according to the present invention, using samples of whole dried blood on an absorbing paper, is superior to the serum hormone assays in the following ways:

i. the minute amounts of blood required by the method;
ii. the simplicity of sample collection, by either medical or non-medical personnel;
iii. absence of risk of accidental loss of samples by breakage of glass tubing;
iv. absence of need to centrifuge blood samples;
v. convenience of sample delivery by surface or air mail in an envelope;
vi. convenience of sample storage;
vii. practical application of this method for the measurement of specific steroids in mass screening programs.

For transferring the blood sample to the absorbing material according to the present invention, a blood sample can be collected directly onto a sheet of absorbing material from a small cut, for example, in the finger tip of a patient or by means of heel prick from a newborn infant. Of course, a small portion of a larger blood sample, which has been drawn from a human being directly into a heparinized tube in a conventional manner, can also be transferred onto an absorbing sheet to be used in the present test method.

The necessary amount of body liquid, in particular blood, which is used in the present test method, of course, varies, depending on the respective steroid which is to be tested, the sensitivity of the antiserum which is available for this steroid and the condition of the patient to be diagnosed, e.g., the expected level of the steroid in the body liquid of the patient. For example, to detect an abnormally increased level of dehydroepiandrosterone sulfate in blood, an amount of from about 10 to about 20 $\mu l$ is preferably used. The absorbing material is preferably a uniformly absorbing filter paper. Example of suitably absorbing papers are filter paper No. 903 of Schleicher and Schuell or the standard absorbing paper which is used for collecting blood samples in the hospital as a standard procedure for neonatal screening for phenylketonurea. Such filter paper can absorb only a certain amount of liquid per surface area unit. When the body liquid, e.g., blood, is dropped gently on the filter paper, a standard size of filter paper disc will contain a standard amount of the liquid. Therefore, an identical volume of test samples of the body liquid, e.g., the blood, in various tests, can be insured by using the same kind of absorbing paper and punching out a a standard size disc of the dry blood-containing absorbing paper for the recovery of the steroid therefrom. It has been found, that the steroids are uniformly distributed throughout the paper area, which has been impregnated with the body liquid, e.g., the blood.

For eluting the steroid from filter paper containing dried whole blood, the latter is treated with an aqueous eluant. Water or aqueous salt solutions may be used as eluants. The eluant preferably is an aqueous buffer solution, having a pH-value of from about 6 to about 8, e.g., a sodium monophosphate/sodium diphosphate buffer solution. In order to effectively elute the whole amount of blood sample impregnated on the absorbing sheet, the elution preferably takes place at a temperature at 25° C., and then the steroid-containing eluate is subjected to a conventional radioimmunoassay test for determining the amount of the steroid therein.

The steroid-containing eluate is suitable for a radioimmunoassay determination of the amount of a steroid thereon, and optionally further purification of the steroid-containing eluate is possible, by extracting steroids with an organic solvent and conventional chromatographic methods, in order to eliminate components therein which will interfere with the radioimmunoassay test. Whether and to what extent a further purification of the steroid-containing eluate is necessary will depend on the selectivity (specificity) of the antiserum which is available for the steroid which is to be determined.

The conventional separation of the plasma from the hematocrit (=mass of the blood cells) of the blood sample is omitted in the method according to the present invention, as no interference from hematocrit components, e.g., from erythrocytes, is observed in the radioimmunoassay determination of the steroid. Further, it has been established that standard size of absorbing sheet contains a standard amount of serum or whole blood.

Radioimmunoassay techniques for the determination of the various steroid hormones are well known in the art. The steroid-containing eluates from body liquids, e.g., blood samples, which have been treated according to the present invention, can be tested in any of these conventional radioimmunoassay tests in the same manner as steroid fractions which have been recovered from body liquids, in particular blood plasma in a conventional way.

For example, to determine the dehydroepiandrosterone sulfate content of a blood sample according to the present invention, a sufficient solution of a known amount of radioisotopically labeled dehydroepiandrosterone sulfate, e.g., dehydroepiandrosterone (7-$^3$H, net-033) in the same buffer solution and a sufficient solution of an amount of the antiserum for dehydroepiandrosterone sulfate in the same buffer solution is added to the steroid-containing eluate to bind an important portion, preferably between about 30 and about 50% of the radioisotopically labeled dehydroepiandrosterone sulfate.

In order to allow the formation of the steroid-antibody-complex, the mixture is incubated at about ambient temperature for a period of about 178 -2 hours and subsequently at ice bath temperature for a further period of about 30 minutes or overnight incubation at 40° C. (>12 hours). Subsequently, the free steroids are separated from the steroid-antibody-complex in a conventional manner, preferably by means of charcoal adsorption, and the radioactivity of the remaining steroid-antibody-complex solution is determined.

Finally, in another embodiment of the invention, there is provided a means for the determination of a steroid hormone in a sample of a human body liquid, comprising a first container, having therein (a) an absorbing paper, adapted for absorbing a sample of the human body liquid;

(b) a second container, containing a first reagent, which comprises a radioisotopically labeled form of the steroid hormone; and (c) a third container, containing a second reagent, comprising an antiserum for the steroid hormone.

In order to more fully describe the present invention, the method for determining the blood levels of dehydroepiandrosterone sulfate utilizing the present invention is described below. It is understood that the specific procedure is intended merely to be illustrative and in no sense limiting.

The dehydroepiandrosterone sulfate content in various samples of venous blood and of capillary blood of any subject is determined by the method according to the present invention, using blood elution from filter paper and in a conventional manner by using the plasma-fraction of the blood.

EXAMPLE 1

Specimens of whole venous or whole capillary blood from health volunteers and patients with endocrine disorders are analyzed. The dehydroepiandrosterone sulfate content is determined by radioimmunoassay in samples of the whole blood according to the method of the present invention and in samples of the plasma from the same whole blood.

1. Preparation in duplicate, of the whole blood sample for the radioimmunoassay to evaluate blood volume in the ⅛ inch disc specimen:

(a) 5 µl of the blood is pipetted onto a piece of filter paper no. 903 of Schleicher and Schuell, or filter paper used for screening for phenylketonurea:

(b) a drop of unknown volume of the same blood is put onto a second piece of the same filter paper;

(c) after the blood has dried, the entire blood-impregnated area of the piece of filter paper, which has been impregnated with 5 µl blood sample, is cut out and dropped into an extraction tube and a disc of ⅛-inch diameter from the blood impregnated area of the second filter paper piece is punched directly into another extraction tube by means of a paper puncher;

(d) 500 µl of a 0.01 M sodium/monophosphate/sodium diphosphate buffer solution, containing 0.1% of gelatin and 0.01% of sodium azide (=assay buffer solution) or distilled water is added to each of the extraction tubes. The tubes are then allowed to stand at room temperature for 15 to 30 minutes;

(e) aliquots of the resulting mixture are directly subjected to the radioimmunoassay test.

2. Preparation in duplicate, of the comparative plasma sample for the radioimmunoassay: The plasma is separated from the whole blood in a conventional hematocrit centrifuge and is diluted with the assay buffer solution or distilled water. An amount of the plasma-dilution, which is equivalent to 2.5 µl of plasma, is pipetted into an extraction tube and the volume of the plasma-dilution is brought up to 500 µl with the above buffer solution or distilled water aliquots of the resulting mixture are directly subjected to the radioimmunoassay test.

3. Radioimmunoassay:

Reactants:

Antiserum for dehydroepiandrosterone sulfate purchased from Dr. Guy Abraham of Harbor General Hospital, Torrance, Calif.

Radiolabeled dehydroepiandrosterone (DHA) (7-$^3$H, net-033) (specific activity 25 Ci/mM) obtained from New England Nuclear.

Plasma blanks, containing no detectable amounts of dehydroepiandrosterone sulfate are obtained by treating plasma with dextran-coated charcoal (stripped plasma).

Whole blood blanks, dried on filter paper or whole blood itself, containing no detectable amounts of dehydroepiandrosterone sulfate are obtained from prepubertal patients undergoing dexamethasone administration.

All blanks are prepared as described above.

Test procedure

Known amounts of added labeled dehydroepiandrosterone sulfate (=DHA) in plasma and in filter paper specimens in quadruplicate were diluted with buffer solution and assayed. To study accuracy, known amounts of added unlabeled dehydroepiandrosterone sulfate were added to plamsa and to whole blood filter paper specimens in duplicate and assayed.

Standards and samples containing antibody and labeled hormone were incubated at room temperature for 1½ hour and then placed in an ice bath for 15 to 30 minutes. Subsequently. 0.5 ml of charcoal dextran (=a suspension of 0.25% charcoal, 0.25% dextran in assay buffer solution stored at 4° C.), is added at 4° C. temperature. The mixture is briefly vortexed, incubated for 10 minutes and centrifuged at 4° C. at 3000 rpm for 10 minutes.

A standard curve is prepared with a range of concentrations between 0 and 10,000 pg, including diluted high standard steroid concentration.

The results are given in Tables I-VI below.

As depicted in Table I, dehydroepiandrosterone sulfate concentrations were below the sensitivity of the standard curve for blank specimens of plasma and filter paper eluate of whole blood as well as in the hemolysate or 20 μl of washed, packed red blood cells. This indicates an absence of a non-specific effect by either the red blood cells or the filter paper substance in the assay system.

Evaluation of the assay

The sensitivity of the standard curve, which was defined as the smallest amount of steroid standard which displaced labeled steroid significantly (P less than 0.001) was 19±4.2 pg as depicted in Table I.

The mean (±1 S.D.) percent recovery of added hormone to the filter paper blanks and plasma blank specimens were 101%±8 and 96%±10, respectively, as seen in Table II. The mean (±1 S.D.) recovery of varying concentrations of added unlabeled hormone in plasma blank preparations and dried filter paper blood preparations were 96%±10 and 114%±24, respectively, as shown in Table II. The inter-assay and intra-assay coefficient of variation for whole blood filter paper spots and for plasma samples does not exceed 13%, 11.4%, respectively.

To test the effect of time (days) and temperature, samples of dried whole blood on filter paper were stored at room temperature, and a ⅛-inch disc was obtained at 0, 7, 14, 21, and 30 days. The stability of the hormone in dried blood on filter paper specimens in five blood samples with varying steroid concentrations indicate that the concentration of steroid in the dried blood on filter paper remains substantially unchanged with a coefficient of variation less than 19% as illustrated by Table III.

The evaluation of plasma volume in the ⅛-inch disc of filter paper specimens is depicted in Table IV where an $^3$H steroid was dissolved into whole blood samples with varying hematocrits and subsequently applied to filter paper from which a ⅛-inch disc was removed. Plasma from the remaining blood samples was separated and eluates of plasma aliquots (20 μl) and filter paper discs (⅛-inch) had radioactivity counts performed thereon. Plasma volume was calculated by comparing radioactivity measured in the disc samples to that of the plasma aliquots and the results indicate that a constant amount of plasma (1.44 to 1.90 μl; 1.72 μl in mean value) is absorbed by the standard size disc (⅛-inch), regardless of the red blood cell mass.

Table V depicts calculation of plasma volume in ⅛-inch discs of whole blood filter paper with varying hematocrits by RIA determination of steroid concentrations. Plasma volume (1.34 to 1.75 μl in mean value) in the ⅛-inch disc was similar to that obtained from the study of the recovery of radio-labeled steroid depicted by Table IV.

The comparison of steroid concentrations in simultaneously obtained venous and capillary blood samples is illustrated by Table IV, illustrating that the concentration was similar in both venous and capillary blood. To calculate plasma steroid concentrations in the disc samples, the mean plasma volume (1.66 μl) of the ⅛-inch disc from the study as shown in Tables IV and V, was used.

TABLE I

| Assay | n | Read in 20 μl plasma blank (pg) | Read in 20 μl of whole blood on filter paper eluate blank (pg) | Read in hemolysate of 20 μl of packed washed red blood cells (pg) | Lowest limit (pg) of sensitivity in standard curve |
|---|---|---|---|---|---|
| DS | 10 | 7.1 ± 3.6 | 7.0 ± 4.4 | 8.0 ± 3.3 | 19.0 ± 4.2 |

TABLE II

| | No. of Trials | Steroid added (pg) | PERCENT RECOVERY Plasma blank | PERCENT RECOVERY Whole blood blank on filter paper |
|---|---|---|---|---|
| $^3$H-labeled DHA | 7 | — | 96 ± 10.1 | 101 ± 8.0 |
| DS | 10 | 50 | 96 ± 10 | 114 ± 24 |
| | 10 | 250 | 95 ± 13 | 107 ± 6 |
| | 10 | 500 | 92 ± 12 | 100 ± 12 |
| | 10 | 1000 | 84 ± 8 | 88 ± 7 |

TABLE III

| Hormone | Sample | Steroid concentration (pg per ⅛ inch disk due at 25° C.) | | | | | Coefficient of variation (%) |
| --- | --- | --- | --- | --- | --- | --- | --- |
| | | Day 0 | Day 7 | Day 14 | Day 21 | Day 30 | |
| DS | 1 | 153 | 158 | 179 | 152 | 133 | 10.5 |
| | 2 | 2,780 | 3,547 | 3,871 | 3,288 | 3,856 | 13.0 |
| | 3 | 15,050 | 10,465 | 10,724 | — | 10,546 | 19.0 |
| | 4 | 19,942 | 19,018 | 18,387 | 19,229 | 13,122 | 15.0 |

TABLE IV

| Steroid | Sample | Hematocrit % | $^3H$ (cpm) | | Calculated plasma volume (μl) in ⅛" disc |
| --- | --- | --- | --- | --- | --- |
| | | | 20 μl of plasma | whole blood in ⅛" disc | |
| DS | 1 | 27 | 2,456 | 220 | 1.79 |
| | 2 | 34 | 1,569 | 113 | 1.44 |
| | 3 | 36 | 2,951 | 268 | 1.81 |
| | 4 | 40 | 2.858 | 272 | 1.90 |
| | 5 | 44 | 3,142 | 249 | 1.58 |
| | 6 | 46 | 3,229 | 288 | 1.78 |
| | | | | | Mean ± S.D. 1.72 ± 0.17 |

TABLE V

| Steroid | Sample | Hematocrit (%) | Measured steroid (pg) | | Calculated plasma volume (μl) in ⅛" disc |
| --- | --- | --- | --- | --- | --- |
| | | | 20 μl plasma | Whole blood in ⅛" disc | |
| DS | 1 | 30 | 614 | 54 | 1.75 |
| | 2 | 31 | 162 | 12 | 1.48 |
| | 3 | 35 | 254 | 21 | 1.65 |
| | 4 | 42 | 180 | 14 | 1.55 |
| | 5 | 48 | 934 | 63 | 1.34 |
| | 6 | 51 | 1,010 | 70 | 1.38 |
| | | | | | mean ± S.D. 1.52 ± 0.15 |

TABLE VI

| Steroid | Subject | Venous Blood | | Capillary Blood | | Coefficient of variation (%) |
| --- | --- | --- | --- | --- | --- | --- |
| | | Plasma | Eluate of ⅛" disc | Plasma | Eluate of ⅛" disc | |
| DS | 1 | 248 | 220 | — | 228 | 4.3 |
| | 2 | 203 | 236 | — | 185 | 12.4 |
| | 3 | 403 | 453 | — | 414 | 6.2 |

We claim:

1. A method for determination of a steroid in a sample of a human body liquid which comprises the steps of:
   (a) transferring said liquid sample onto a sheet of material which is capable of uniformly absorbing said liquid sample;
   (b) drying the sample-containing sheet;
   (c) treating a portion of the dry sample-containing sheet, which is equivalent to a predetermined amount of the sample with an aqueous solvent in order to obtain a mixture wherein the dried body liquid is substantially redissolved in the aqueous solvent;
   (d) contacting said mixture with an aqueous solution of an agent, capable of selectively binding said steroid in the presence of a radio-isotopically labeled form of the steroid, whereby part of said labeled steroid and part of said unlabeled steroid present in the sample are bound by forming a complex with said binding agent, separating said bound steroids from unbound steroids in said aqueous solution and measuring the radioactivity of at least said separated binding agent-steroids-complex or said unbound steroids to determine the concentration of said hormone as a function of the measured radioactivity.

2. The method as defined in claim 1, wherein the steroid-binding agent is a steroid-antiserum.

3. The method as defined in claim 1, wherein the steroid is a steroid hormone selected from the group consisting of adrenal and gonadal sex steroids and corticosteroids.

4. The method as defined in claim 3, wherein the steroid is selected from the group consisting of 17α-hydroxy-progesterone, androstenedione, testosterone, dehydroepiandrosterone, dehydroepiandrosterone-sulfate and cortisol.

5. The method as defined in claim 1, wherein said sample of human body liquid is a sample of whole blood.

6. The method as defined in claim 1, wherein the steroid is dehydroepiandrosterone sulfate.

7. The method as defined in claim 6, wherein set (d) comprises the steps of:
   (e) mixture adding to the dehydroepiandrosterone sulfate containing mixture an aqueous solution containing a predetermined amount of an antiserum for dehydroepiandrosterone sulfate and an aqueous solution containing a predetermined amount of a radio-isotopically labeled form of dehydroepiandrosterone sulfate which is in excess of the amount which is required to bind said amount of antiserum;
   (f) allowing a steroid-radioactive steroid-antiserum-complex to form in the aqueous solution;
   (g) separating the unbound steroids from the aqueous solution of (f), and
   (h) determining the content of radioactivity of radio-isotopically labeled steroid in the aqueous solution.

8. The method as defined in claim 7, wherein said radioisotopically labeled dehydroepiandrosterone sulfate is labeled with $^3H$.

9. The method as defined in claim 8, wherein said blood sample is of a newborn infant, suspected of being affected by congenital adrenal hyperplasia and whereby the results of that method provide a determination of the condition (diagnosis and therapeutic responsiveness) of congential adrenal hyperplasia for any age group of the patient.

10. The method as defined in claim 7, wherein said blood is utilized in an amount of from about 5 to about 20 μl for the diagnosis of congenital adrenal hyperplasia.

11. A method for detecting functional disorders in the human body, which result in an increased level of at least one steroid hormone in a human body liquid, which comprises the steps of subjecting a sample of the human body liquid to the method as defined in claim 1.

12. A method for detecting congenital adrenal hyperplasia in newborn infants, which comprises the steps of collecting a blood sample of the newborn infant on a sheet of absorbing material and subjecting this blood sample to the method as defined in claim 7.

13. A method as defined in claim 11, comprising detecting abnormal adrenal androgen secretion.

* * * * *

UNITED STATES PATENT AND TRADEMARK OFFICE
CERTIFICATE OF CORRECTION

PATENT NO. : 4,431,743

DATED : February 14, 1984

INVENTOR(S) : Songja PANG and Maria NEW

It is certified that error appears in the above—identified patent and that said Letters Patent is hereby corrected as shown below:

IN THE BIBLIOGRAPHICAL DATA:

Item [63] under the heading of "RELATED U.S. APPLILCATION DATA", kindly delete "abandoned" and insert instead -- issued as U.S. Patent No. 4,230,684 on October 28, 1980. --

Column 1, lines 9-11, kindly delete "copending patent application Ser. No. 887,326, filed Mar. 16, 1978, abandoned and" and insert instead -- U.S. Patent Application Ser. No. 887,326, filed Mar. 16, 1978, now U.S. Patent No. 4,230,684, issued October 28, 1980, --.

UNITED STATES PATENT AND TRADEMARK OFFICE
CERTIFICATE OF CORRECTION

PATENT NO. : 4,431,743
DATED : February 14, 1984
INVENTOR(S) : Songja PANG and Maria NEW It is certified that error appears in the above—identified patent and that said Letters Patent is hereby corrected as shown below:

Column 5, line 64, kindly delete "178" and insert instead -- 1/2 --.

Signed and Sealed this

Thirty-first Day of July 1984

[SEAL]

Attest:

Attesting Officer

GERALD J. MOSSINGHOFF

Commissioner of Patents and Trademarks